United States Patent [19]

Spierer et al.

[11] 4,155,455

[45] May 22, 1979

[54] EDDY CURRENT AND VARIABLE RELUCTANCE TEST APPARATUS FOR ROLLERS AND THE LIKE

[75] Inventors: Edward D. Spierer, Belle Harbor; Paul J. Bebick, Bronx; Peter J. Suhr, Westbury, all of N.Y.

[73] Assignee: Magnetic Analysis Corporation, Mount Vernon, N.Y.

[21] Appl. No.: 830,886

[22] Filed: Sep. 6, 1977

[51] Int. Cl.$^2$ .............................................. B07C 5/344
[52] U.S. Cl. .................................... 209/558; 209/570; 209/701; 209/916; 324/232
[58] Field of Search .................. 209/71, 72, 73, 74 R, 209/74 M, 75, 81 R, 81 A, 111.8, 558, 567, 570, 571, 701, 916, 555; 324/238, 232, 240–242, 237

[56] References Cited

U.S. PATENT DOCUMENTS

| | | | |
|---|---|---|---|
| 2,441,380 | 5/1948 | Zuschlag | 324/232 X |
| 2,989,179 | 6/1961 | Woods et al. | 209/81 R X |
| 3,271,664 | 9/1966 | Mountz et al. | 324/232 X |
| 3,355,014 | 11/1967 | Howles | 209/73 |
| 3,538,433 | 11/1970 | Wood et al. | 324/232 X |

*Primary Examiner*—Robert J. Spar
*Assistant Examiner*—Edward M. Wacyra
*Attorney, Agent, or Firm*—Pennie & Edmonds

[57] ABSTRACT

Non-destructive testing apparatus for rollers and the like of magnetic material comprises a pair of rotating spin rails having intermediate sections of magnetic material. Feeding apparatus deposits rollers on the spin rails and moves them successively past the magnetic sections. A magnet produces flux through the magnetic sections and a roller rotating thereon. Variable reluctance sensing apparatus senses changes in the flux. An eddy current test probe is positioned adjacent the magnetic sections. Variable reluctance and eddy current test circuits produce flaw output signals which control apparatus for segregating the rollers. Advantageously the feeding apparatus intermittently deposits successive rollers on the spin rails and intermittently moves the rollers along the rails in end-to-end relationship. Flaw signals are stored and utilized for segregation after a predetermined number of intermittent movements of the rollers to an ejection station where they are raised and deflected from the spin rails into segregating chutes. Particular feeding apparatus using a channeled head movable over a slot are described. In a modification for testing tapered rollers, a cam follower and guide tapered roller maintain a constant spacing of the eddy current probe from the roller under test. Timing apparatus are described for making the eddy current test during forward movement of a roller past the probe, and the variable reluctance test during intervals between the forward movements.

16 Claims, 15 Drawing Figures

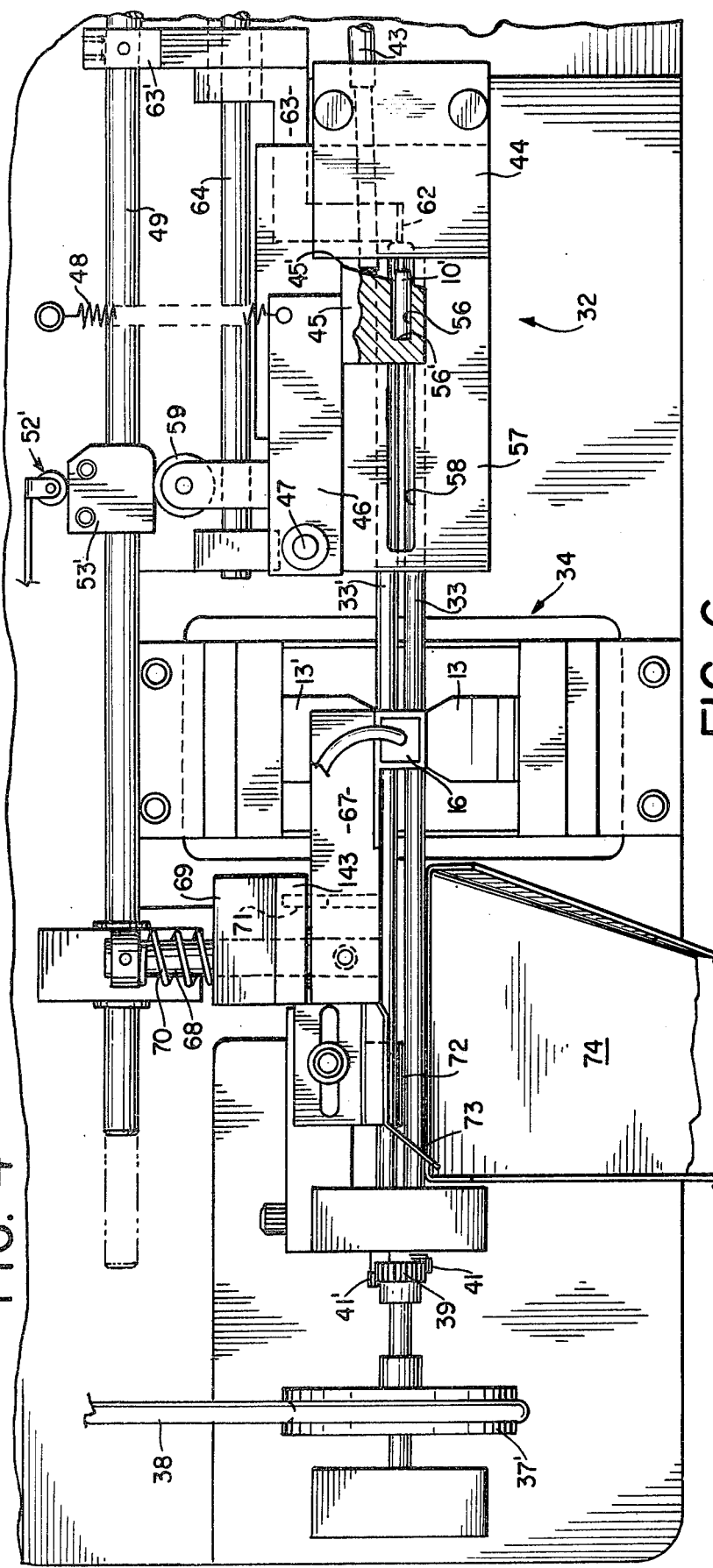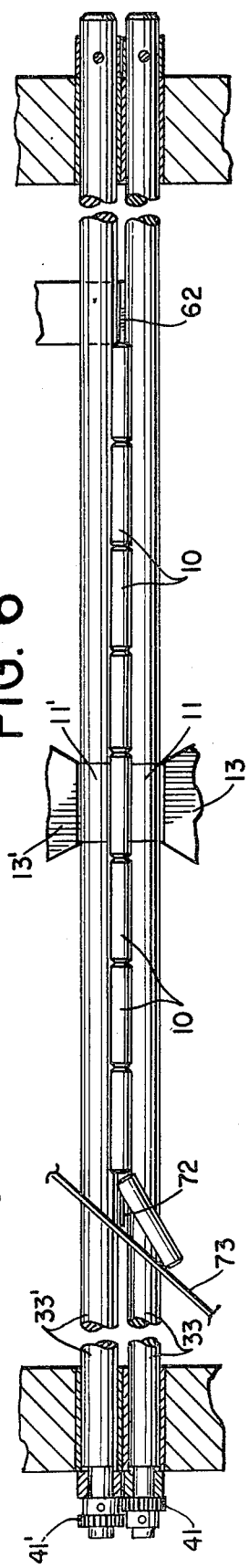

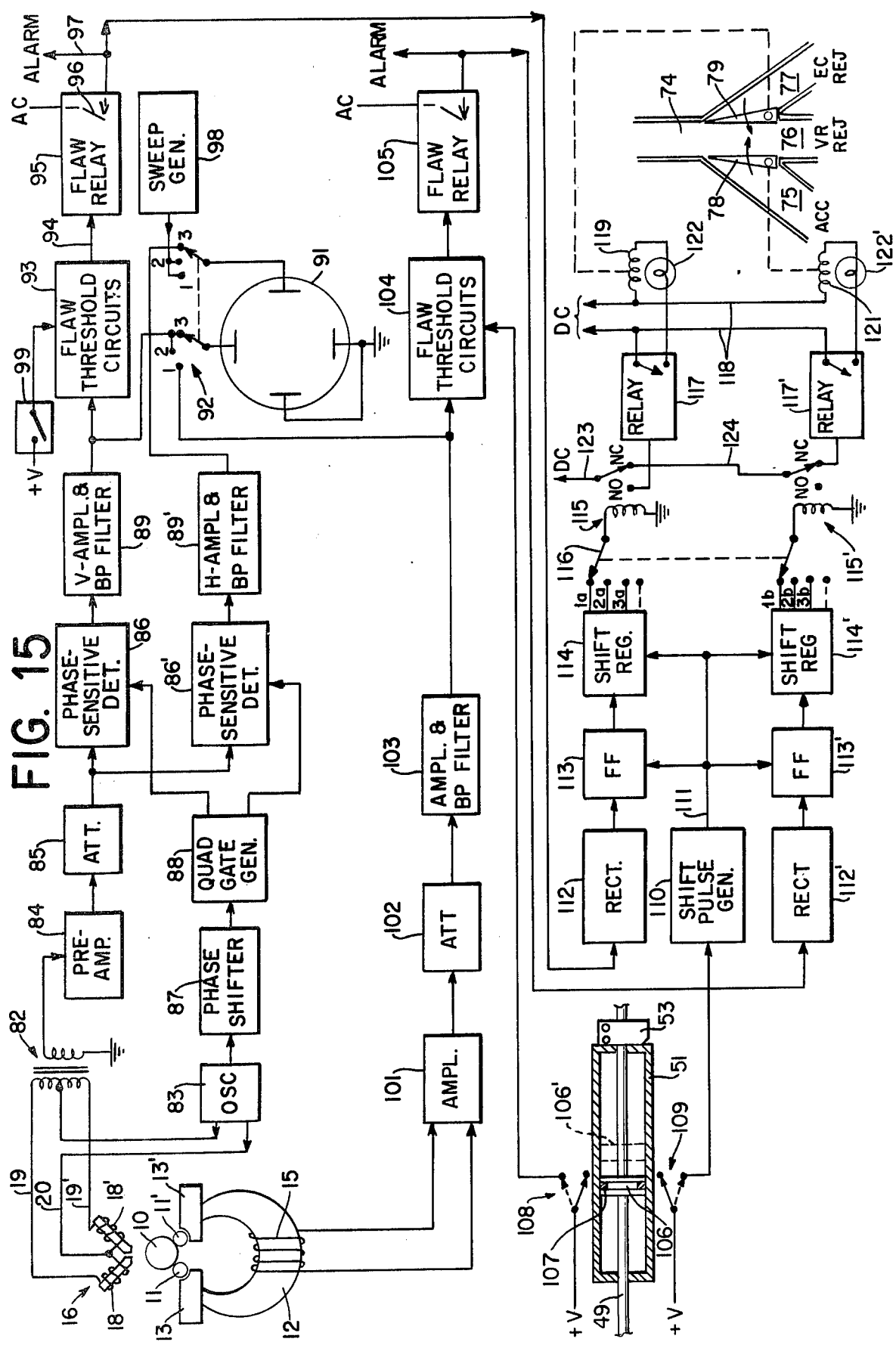

EDDY CURRENT AND VARIABLE RELUCTANCE TEST APPARATUS FOR ROLLERS AND THE LIKE

This invention relates to non-destructive testing apparatus for rollers and the like of magnetic material, and particularly to apparatus for performing eddy current and variable reluctance tests thereon.

It is frequently important to test rollers and the like of magnetic material for defects or flaws therein which could affect their performance and durability in use, for example steel rollers used in roller bearings. Testing for both surface and subsurface defects is highly desirable.

Eddy current tests are particularly suitable for detecting surface flaws. The depth of penetration of eddy currents in ferromagnetic materials is, however, limited by the permeability of the material, as well as by the conductivity of the material and the test frequency employed. The depth of penetration is commonly considered to be equal to $1/\sqrt{\pi f \sigma \mu}$ where f is the test frequency, $\sigma$ is the conductivity, and $\mu$ is the permeability of the material. At test frequencies of say, 67 KHz or 200 KHz, the depth of penetration may be only one or a few mils. In order to detect sub-surface defects, the present invention employs a variable reluctance test.

In accordance with the invention, a pair of rotating spin rails are employed for rotating a roller to be tested. The spin rails have respective intermediate sections of magnetic material at like positions along the length thereof, for example, midway of the length of the rails. Eddy current and variable reluctance tests are made on a roller while it is rotating on the intermediate magnetic sections of the spin rails. Magnetic means, preferably a permanent magnet, are positioned adjacent the magnetic sections and produce magnetic flux through the magnetic sections and the roller rotating thereon. Variable reluctance sensing means, advantageously a coil wound around the permanent magnet, sense changes in the flux due to a defect or flaw in the roller as it rotates in the magnetic field, and test circuits connected with the sensing means produce a flaw signal.

An eddy current test probe is positioned adjacent the intermediate magnetic sections of the spin rails and performs an eddy current test on the rotating roller. The probe is connected to eddy current test circuits which produce a flaw signal if a defect or flaw is detected.

Several advantages result from performing the eddy current test while the roller is at the magnetic sections of the spin rails. The magnetic field magnetically clamps the roller to the rails so that high rotational speeds may be employed without bouncing of the roller, hence improving the signal to noise ratio of flaw signals. Also, the magnetization of the roller reduces the effect of changes in permeability of the roller which would adversely affect the eddy current test. Leakage flux associated with a surface defect may also sharpen the flaw signal.

In further accordance with the invention, feeding means are provided for depositing rollers on the spin rails and moving the rollers successively past the intermediate magnetic sections, and segregating means are provided for segregating the rollers in accordance with the presence or absence of flaw signals for respective rollers.

The feeding means advantageously includes a plate having a slot therein extending longitudinally over the spin rails, and a movable feed head over the plate having a channel closed at one end and open at the bottom. The feed head has receiving and feeding positions in which the channel is respectively away from and over the slot. Supply means aligned with the channel in the receiving position supplies rollers longitudinally into the channel to abut the closed end thereof. The head is alternately moved between the receiving and feeding positions to drop received rollers into the slot in succession.

For some applications the width of the slot is predetermined to allow a roller to drop therethrough onto the spin rails, and a feed finger intermittently advances the rollers as they are dropped onto the rails. In other applications the rollers may be sufficiently large and heavy so that direct dropping onto the spin rails might mar the surface finish of the rollers, or unduly wear the rails. In such cases the slot is at least partially closed at the bottom to hold a roller slightly above the spin rails, and a feed finger intermittently advances the rollers until they drop from the bottom of the slot onto the rails.

Preferably the rollers are moved along the rails in end-to-end relationship, and are removed in succession from the rails beyond the intermediate magnetic sections, advantageously by an inclined ramp between the rails which raises the leading roller, and an angled member which deflects the raised roller off the rails.

Flaw signals produced while the rollers are at the intermediate magnetic sections are stored, and means responsive to a predetermined number of intermittent movements of the rollers along the rails are provided to utilize the stored signals to segregate rollers as they are removed from the rails.

For testing tapered rollers and the like, mounting means are provided for the eddy current probe which is designed and adapted for moving the probe toward and away from a roller on the spin rails. Cam follower means coupled with the probe mounting means is provided, and includes means for holding a guide tapered roller of like taper to those being tested. Means are provided for producing relative movement between the guide roller and the cam follower synchronously with movement of a roller past the probe for maintaining a substantially constant spacing of the probe with respect to the roller under test.

Other features and advantages of the apparatus of the invention will be apparent from the following description of specific embodiments thereof.

BRIEF DESCRIPTION OF THE DRAWINGS

FIG. 4 is an enlarged plan view of a portion of FIG. 2;

FIG. 6 is a detail illustrating the end-to-end feeding of rollers being tested;

FIG. 15 illustrates control circuits of the apparatus.

DESCRIPTION OF THE SPECIFIC EMBODIMENTS

Figure 1:
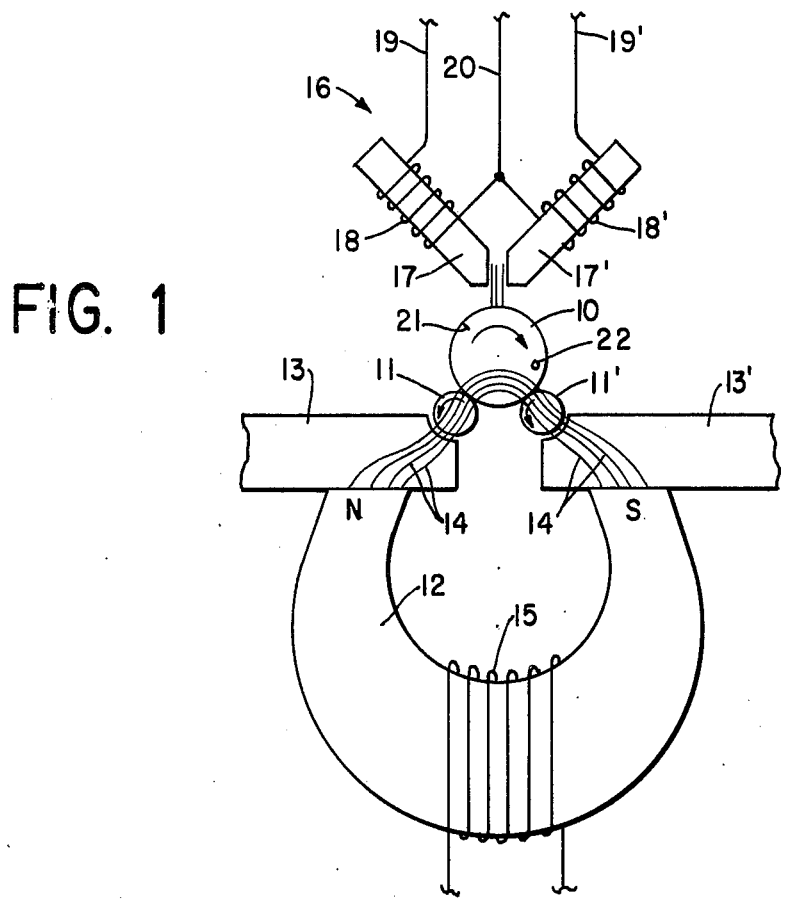
FIG. 1 is a detail illustrating variable reluctance and eddy current testing of a roller in accordance with the invention.

Referring to FIG. 1, the principles of the variable reluctance and eddy current tests are illustrated. A roller 10 being tested is rotated about its axis by a pair of spin rail sections 11, 11', the directions of rotation being indicated by arrows. Sections 11, 11' are of magnetic material, for example, drill rod. A permanent magnet 12 with polepieces 13, 13' produces magnetic flux through sections 11, 11' of the spin rails and the roller 10, as illustrated by lines 14. Coil 15 is wound around the magnet, and the combination serves as a variable reluctance sensing means for sensing changes in the flux. An eddy current probe generally denoted 16 is mounted over sections 11, 11' in position to test roller 10. As specifically shown, a focussed null type probe is employed having ferrite cores 17, 17' with coils 18, 18' wound therearound. Separate leads 19, 19' and a common lead 20 are provided for energizing the probe and picking up flaw signals.

A surface defect or flaw in the roller 10 is indicated at 21. In accordance with eddy current testing principles, an alternating or pulse energizing signal to the probe produces eddy currents in and adjacent the surface of roller 10, and when flaw 21 passes under the probe the eddy current flow will be disturbed. Thus a flaw signal will be produced each revolution of the roller.

A sub-surface defect is indicated at 22. As the roller 10 rotates, defect 22 will pass into the flux field and increase the reluctance of the magnetic circuit. Thus the flux will be reduced as the defect enters the flux field, and will increase as the defect leaves the field. The change in flux induces a voltage in coil 15 which is amplified and processed to produce a flaw signal. Usually there will be two flaw signals per revolution of the roller, as the flaw passes over the two spin rails in succession.

Any bouncing of roller 10 would produce signals in the eddy current probe which would mask signals due to flaws. Inasmuch as the magnetic field holds the roller tightly against the spin rail sections, such bouncing is prevented and the flaw sensitivity improved. Also, high rotational test speeds may be employed to promote rapid testing. Further, there may be spots in roller 10 of different permeability than adjacent portions, thus giving rise to false flaw signals or noise. The presence of the magnetic field during the eddy current test tends to reduce such extraneous signals, and improves the signal to noise ratio for an actual flaw. In addition, there may be some flux leakage in the vicinity of a surface flaw such as 21 which will sharpen the eddy current flaw signal. It should be noted that the flux lines 14 are for illustrative purposes only, and additional flux lines will exist depending on the magnetic properties, dimensions, etc. of the materials involved.

Figure 2:
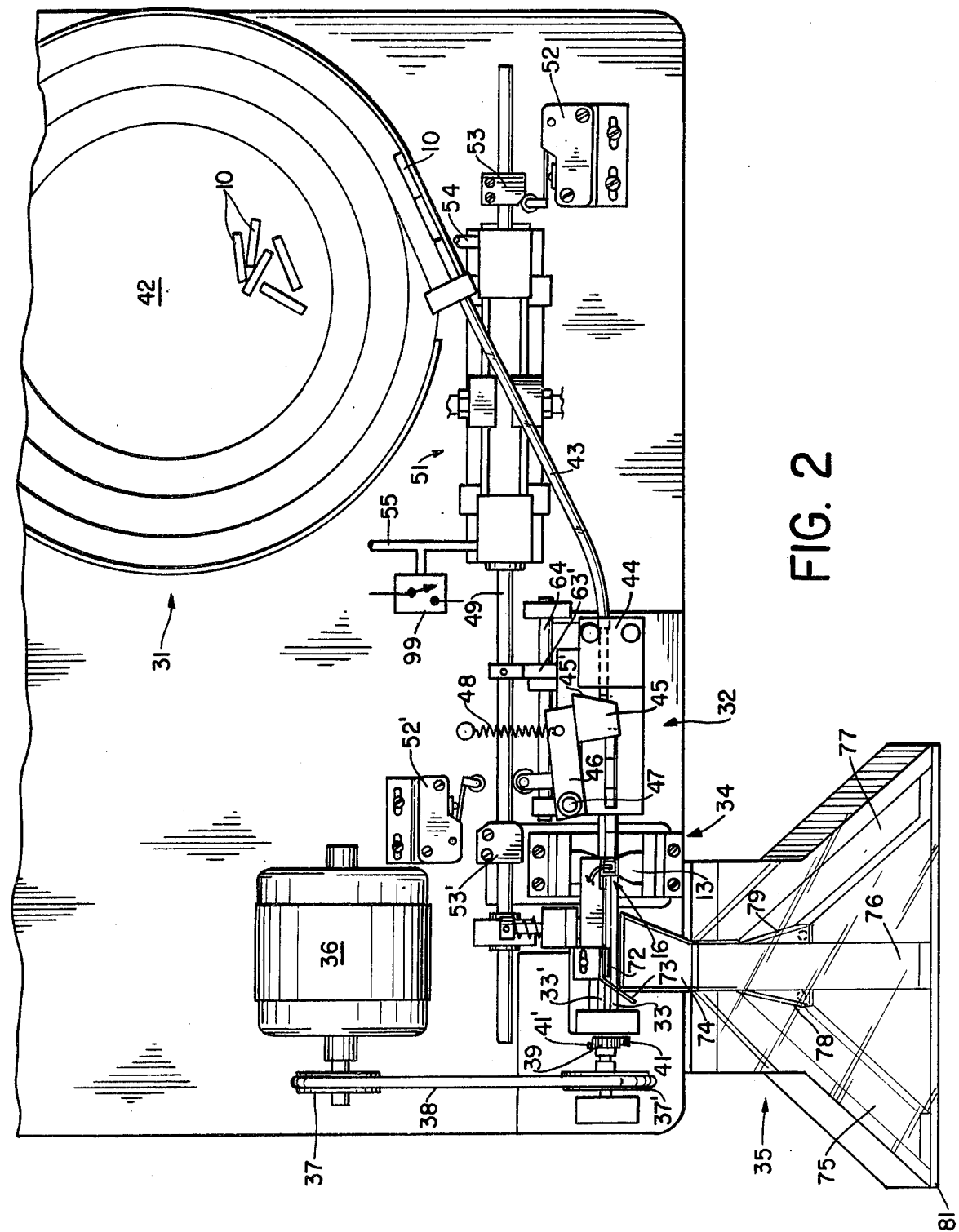
FIG. 2 is a plan view of testing apparatus in accordance with the invention.
Figure 3:
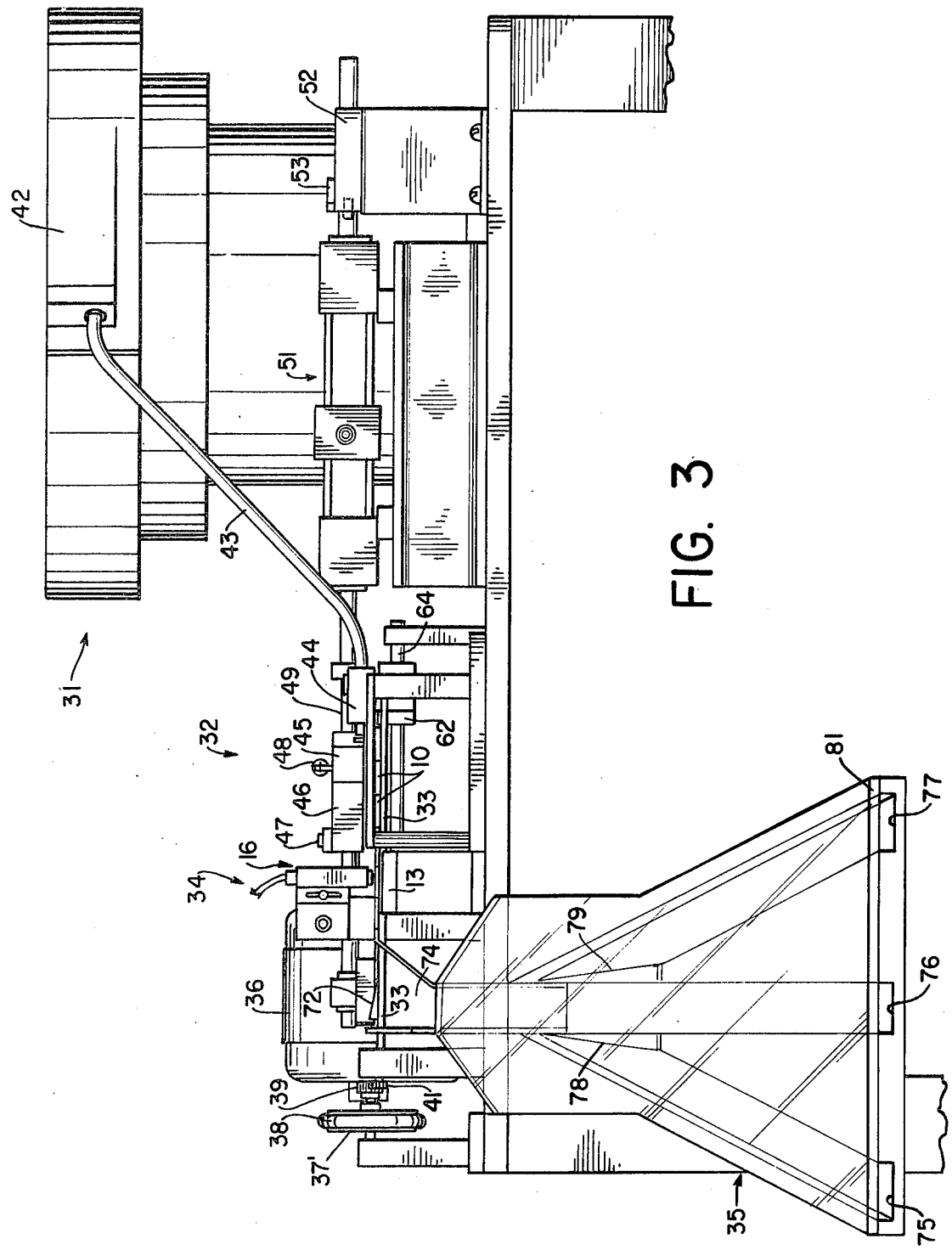
FIG. 3 is an elevation of the apparatus of FIG. 2.

Referring to FIGS. 2 and 3, roller supply means generally designated 31 supply the rollers 10 to be tested to a feed station generally designated 32 which deposits the rollers on the spin rails 33, 33' and moves the rollers successively past the test station generally designated as 34 where the intermediate magnetic sections 11, 11' (FIG. 1) are located. Eddy current and variable reluctance tests are made at the test station 34. After passing the test station, the rollers 10 are removed from the spin rails and segregated by means generally designated 35.

Advantageously, except for the intermediate magnetic sections 11, 11', the spin rails are of non-magnetic material, for example stainless steel, to avoid flux leakage. As a given roller leaves the test station, it is automatically demagnetized by its spinning motion in the decreasing magnetic field.

Figure 7:
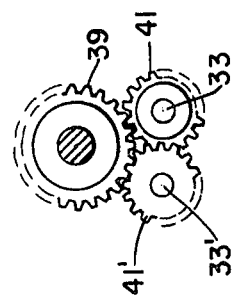
FIG. 7 is a detail illustrating the gear drive of the spin rails.

The spin rails 33, 33' are driven by motor 36 through pulleys 37, 37' and belt 38. Pulley 37' is affixed to a shaft on which gear 39 is affixed. As best seen in FIG. 7, gear 39 meshes with gears 41, 41' affixed to spin rails 33, 33' respectively. Thus gear 39 drives the spin rails in the same direction of rotation, as indicated in FIG. 1.

The roller supply means 31 as here shown includes a vibratory hopper 42 of known type. The hopper delivers the rollers 10 in end-to-end alignment through tube 43 to the feed station 32. The end of the tube is held in a stationary block 44. A movable feed head 45 is carried by an arm 46 rotatable about a pivot axis 47 and biased to the position shown by tension spring 48. Rod 49 is reciprocally driven by an air cylinder 51 and a cam affixed to the rod moves arm 46 and feed head 45 alternately between receiving and feeding positions.

Reciprocation of the air cylinder 51 and the piston rod 49 is controlled by air switches 52, 52' actuated by cam blocks 53, 53' adjustably affixed to rod 49. The switches actuate air valves which alternately admit air to opposite ends of the cylinder through tubes 54 and 55. The air valves and control may follow known practices and hence are not shown. The positions of switches 52, 52' are adjustable so that the stroke length of the piston cylinder can be changed for different length rollers to be tested. Preferably the forward stroke of piston rod 49 is determined by a positive stop to assure accurate forward stroke lengths. Cam block 53 serves as a positive stop in the forward direction of travel.

Figure 5:
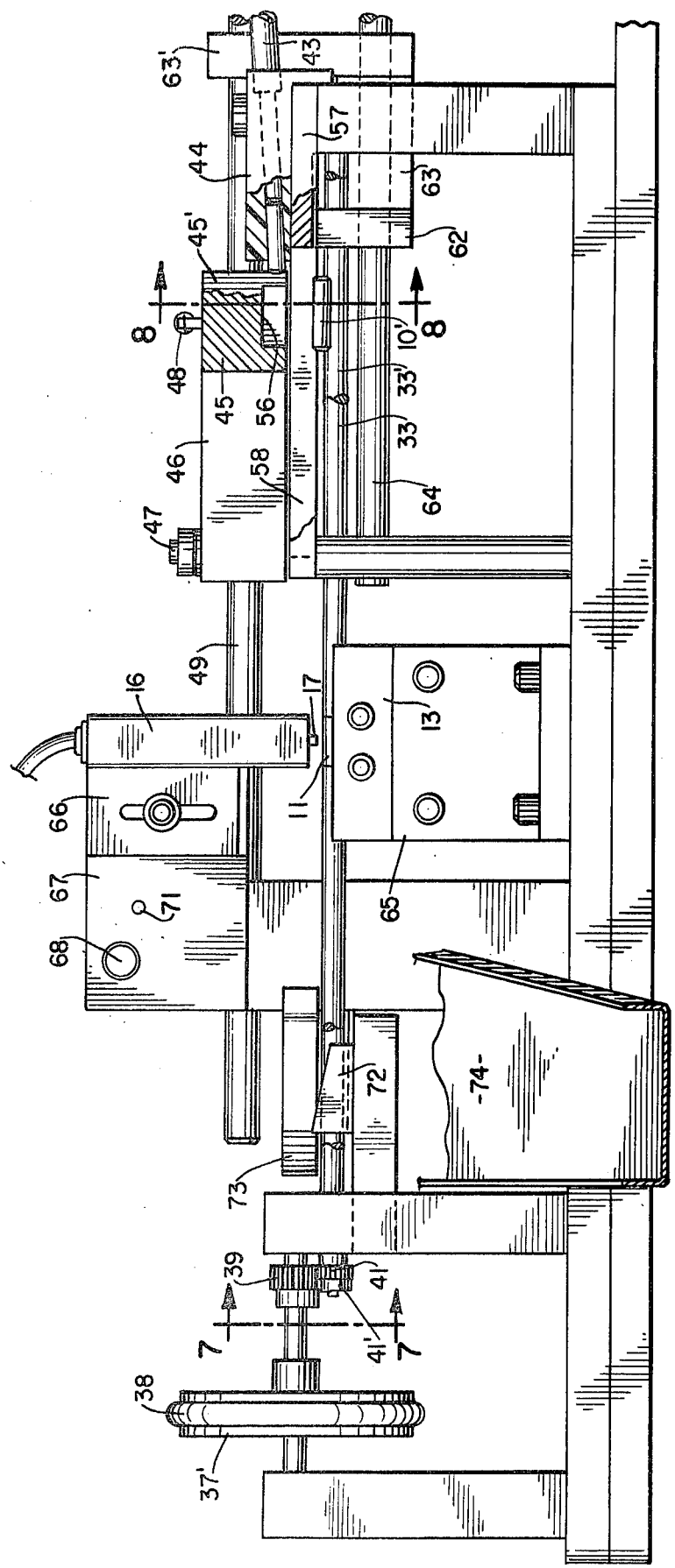
FIG. 5 is an elevation of the portion of the apparatus illustrated in FIG. 4.
Figure 8:
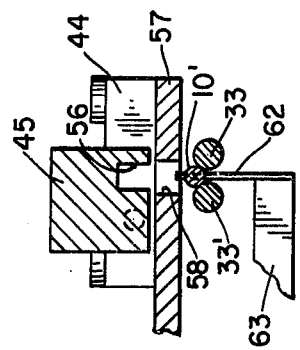
FIG. 8 is a detail of the feed head and slotted plate in feeding position.

Referring to FIGS. 4, 5 and 8, feed head 45 has a channel 56 therein which is closed at one end 56' and is open at the bottom. The head is movable over a plate 57 having a slot 58 therein extending longitudinally over the spin rails 33, 33'. In the receiving position of the head, shown in FIG. 2, channel 56 is in alignment with the roller supply tube 43 and is away from slot 58. The leading roller from tube 43 enters the channel and abuts end 56'. The length of the channel is less than the length of the roller so that the trailing end of the roller projects slightly, and prevents the next succeeding roller from entering the channel. As cam follower 59 (attached to arm 46) is engaged by cam block 53' near the end of the return stroke of piston rod 49, the feed head 45 is moved to its feeding position shown in FIGS. 4 and 8 wherein channel 56 is over slot 58. Accordingly roller 10' drops through the slot onto the adjacent non-magnetic end sections of the spin rails, as shown in FIG. 8. As the head 45 moves away from its receiving position, the next roller from tube 43 abuts the front surface 45' of the head. When the head is returned to its receiving position, the roller enters channel 56, ready for the next feeding movement. The front surface 45' is inclined as shown, so as to be approximately tangential to a radius through the pivot axis 47 of the feed arm, so that the rollers in the tube 43 are not pushed back as the head returns to its receiving position.

If different length rollers are to be tested, the length of channel 56 may be made adjustable, or interchangeable heads employed.

As the rollers are dropped successively onto the spin rails, intermittent means advances them along the rails in end-to-end relationship, as illustrated in FIG. 6. As here shown, a feed finger 62 extends upwardly between the spin rails, and is mounted on a carriage 63 which slides on a guide rail 64 (FIGS. 2,4). A projection 63' of the carriage is affixed to the piston rod 49 of the air cylinder. With the piston rod in its retracted position as shown in FIGS. 4 and 5, feed finger 62 is sufficiently rearward (to the right) of slot 58 so as not to interfere with the dropping of a roller. Then, as the piston rod starts forward and feed arm 46 returns to its receiving position, the feed finger 62 moves forward to advance the roller 10' which has just been dropped onto the spin rails.

Some bouncing of a roller may occur as it drops onto the spin rails and begins to rotate. Accordingly a slight delay is desirable to allow the roller to settle down before it is moved forward. The delay may be produced in the pneumatic controls of known types of air cylinders. Pneumatic valves, containing what are commonly called "spools" in the art, are frequently used to control the admission of high pressure air to each end of the air cylinder, and low pressure air controlled by switches 52, 52' is admitted through needle valves to actuate the spools. By adjusting the needle valves, short delays may be introduced between the closures of the switches and the actual commencement of movement of the piston rod in the opposite direction. In other words, there is a short dwell time between actuation of the air switch and reversal of movement of the piston rod. Preferably a dwell is provided at each end of travel.

As the piston rod reciprocates, at the end of each reverse or retraction stroke a new roller will be deposited on the spin rails at the feed station 32, and during each forward stroke the newly deposited roller will be advanced. Accordingly, as operation continues the rollers will be advanced intermittently in end-to-end relationship as illustrated in FIG. 6, and will move successively past the intermediate magnetic sections 11, 11' of the spin rails to the non-magnetic end sections beyond 11, 11'.

A permanent magnet is positioned at the magnetic sections as illustrated in FIG. 1. FIG. 5 shows a mounting structure 65 for the magnet, and FIG. 4 shows the polepieces 13, 13'. The mounting structure preferably surrounds the magnet and pickup coil structure to act as a shield. The eddy current probe 16 is mounted over the magnetic sections by a plate 66 adjustably secured to a block 67 so that its vertical position can be adjusted for different diameter rollers. Preferably the probe is constructed as a steel housing containing the ferrite cores and coils shown in FIG. 1, so as to provide shielding against extraneous fields. Conveniently block 67 is pivotally mounted by rod 68 in a stationary block 69 so that the probe can be moved out of the way if desired. A spring 70 and detent pin 71 hold block 67, and thus the probe 16, in proper position during operation.

The eddy current test is advantageously made during the forward stroke of the piston rod, during which a roller is moved past the probe. Since the roller is also being rotated by the spin rails, a helical test path is produced. The speeds of forward movement and rotation are selected with respect to the width of the helical test path so that an adequate area of the roller is tested during its passage. Less than complete coverage may suffice, depending on the minimum flaw dimensions it is necessary to detect. In one embodiment using one-quarter inch diameter spin rails, the rails were rotated at about 780 r.p.m. and the longitudinal speed of feeding was about two inches per second.

Advantageously the eddy current test circuits are inoperative during the retract stroke, and also during stroke reversals so that any jars in reversing the piston movement do not create transient signals in the probe which might be falsely indicated as flaws. Suitable timing means will be described in connection with FIG. 15.

In order to detect small surface flaws, the effective width of the eddy current probe in the longitudinal direction of the roller is advantageously small compared to the roller length, and the probe position and feed mechanism are adjusted so that the effective test region of the probe is at the leading end of the roller to be tested as that roller starts to advance. Various positions of the probe along the magnetic sections 11, 11' of the rails are possible. In one embodiment the probe was positioned so that its effective test region registered with the magnetic sections 11, 11' slightly beyond their junctions with the input non-magnetic end sections of the rails.

The timing of the variable reluctance test may be selected as desired to meet the requirements of the particular application. If the length of the rollers under test is equal to or less than the length of the magnetic sections 11, 11', and the feeding is adjusted so that each roller registers with the magnetic sections at the end of the respective forward stroke, the test may be made at the end of the forward stroke and/or during the retract stroke during which the roller does not move longitudinally although it is rotating on the spin rails. For longer rollers, the variable reluctance test may be made during the forward movement of the roller. In general, it is desirable to confine the variable reluctance test to the interval when only the roller under test is at magnetic sections 11, 11', although some overlapping of the magnetic sections by the ends of the preceding and/or succeeding rollers may be acceptable in practice.

After passing the test station, the rollers are removed successively from the spin rails and segregated in accordance with the presence or absence of flaw signals for respective rollers. In the present embodiment, as best seen in FIGS. 4 and 5, a thin plate 72 is positioned between the spin rails and has a sloping upper surface to form an inclined ramp which raises each roller as it nears the ends of the spin rails, and an angled member 73 deflects the roller off the rails. The operation is illustrated in FIG. 6. The deflected rollers drop into a chute section 74.

In the embodiment shown, not only are good rollers segregated from defective rollers, but also the defective rollers are segregated according to whether the defects are detected by the eddy current or variable reluctance tests. If defects in a given roller are detected by both tests, one test overrides the other, and is here selected as the eddy current test.

Chute section 74 leads to three outlet chutes 75, 76 and 77 (FIGS. 2, 3 and 15). Rotatable vanes 78 and 79 direct a given roller to the appropriate outlet chute. The chutes are covered with a transparent plate 81 to insure that rollers do not pop out. For fail-safe operation, and to guard against failure to turn on the test circuits, vanes 78 and 79 are biased to a reject position. As here shown, chute 75 is for acceptable rollers, chute 76 is for rollers which fail the variable reluctance test, and chute 77 is for rollers which fail the eddy current test. Vanes 78 and 79 are biased to the positions shown, so that all rollers are directed to chute 76 if the test circuits are not in proper operating condition.

Before describing certain modifications of the apparatus, the test circuits will be explained.

Referring to FIG. 15, the upper portion illustrates one form of eddy current test apparatus which may be employed. Coils 18, 18' of the probe are connected in a bridge configuration with the center-tapped primary of transformer 82. An energizing signal from oscillator 83, suitably a sine wave, is applied across one diagonal of the bridge and the output signal across the other diagonal is derived by the secondary of the transformer and supplied to preamplifier 84. Balancing circuits may be used between the probe coils and the transformer if desired, in known manner. Different oscillator frequencies may be provided for, and selected as desired.

The amplified signal is supplied through an adjustable attenuator 85 to a pair of phase-sensitive detectors 86, 86'. The output of oscillator 83 is also supplied through an adjustable phase shifter 87 to a quadrature gate generator 88 which produces two gate signals 90° apart. The gate signals are supplied to respective detectors to produce quadrature signal outputs. These outputs are supplied to respective vertical and horizontal amplifiers 89, 89' which may contain band pass filters for selecting the desired bands of the flaw signals. The vertical and horizontal components of the flaw signals may be displayed on a cathode-ray oscilloscope (CRO) 91 in position 3 of switch 92, yielding a polar type display.

The flaw signals from the eddy current test may vary in phase as well as in amplitude, and by adjusting phase shifter 87 the flaw signals may be oriented predominantly in the vertical direction, and noise, etc. predominantly in the horizontal direction.

The output of vertical amplifier 89 is supplied to flaw threshold circuits 93 which may be adjusted to yield flaw signal outputs in line 94 corresponding to signals above a selected amplitude level. These actuate flaw relay 95 to close the switch 96 and actuate an alarm through line 97. The alarm may be a red light, buzzer, etc. For convenience, AC power is employed for the alarm, as indicated.

A linear sweep generator 98 is connected to the horizontal deflection plates of the CRO in positions 1 and 2 of switch 92. In position 2, the output of vertical amplifier 89 is displayed on the linear sweep.

The principles of eddy current testing are well known, and it is believed that the above explanation will suffice. Other types of circuits may be employed if desired.

As previously mentioned, in the embodiment of the present invention it is preferred to make the eddy current measurement during the forward movement of the roller feed mechanism, and to disable the measuring circuits during the retraction of the mechanism and particularly when the piston rod reaches its ends of travel, at which points jars and vibrations may occur. This may be accomplished by inserting a pressure operated switch 99 in the air line 55 of FIG. 2. During forward movement of the piston of the air cylinder 51, the pressure in line 55 is low and switch 99 is open. At the end of the forward travel, the pressure in line 55 goes high to drive the piston in the reverse direction, thus closing switch 99. The switch remains closed until the piston reaches its fully retracted position and the air pressure in line 55 is reduced (and air pressure in line 54 increased) for the next forward stroke.

In FIG. 15, switch 99 is connected between a +V supply voltage and the flaw threshold circuits 93. With the switch open during forward travel, circuits 93 operate as described above. When switch 99 closes, however, the flaw threshold circuits are inhibited from operating.

For the variable reluctance test, the voltage induced in coil 15 by a flaw is amplified in 101, and passed through an adjustable attenuator 102 to amplifier 103. The latter may contain a band pass filter for selecting the desired flaw frequency range. The output is then supplied to flaw threshold circuits 104 which passes signals above a selected threshold level to flaw relay 105 which operates similarly to relay 95 to actuate an alarm if a flaw is detected. The output of amplifier 103 is displayed by the CRO 91 on a linear sweep in position 1 of switch 92.

In order to make the variable reluctance test at the end of the forward travel which registers a roller with the magnetic sections of the spin rails, a magnetically actated switch associated with the air cylinder is employed. A simplified longitudinal cross-section of air cylinder 51 is shown in FIG. 15. Piston 106 has a groove formed therein in which a permanent magnet ring 107 is wrapped. A magnetically actuated switch 108, for example a reed switch, is adjustably mounted outside the air cylinder. In the position shown, the piston is at the end of its forward travel as set by stop 53, and magnet ring 107 actuates switch 108 to its open position as shown in full line. Thus the flaw threshold circuits 104 operate as described above. When the piston and ring magnet are rearward of the forward end of travel, as indicated at 106', switch 108 is closed as shown by the dotted line, and +V is applied to threshold circuits 104 to inhibit their operation. The period during which switch 108 is open (preferably the dwell interval at the end of forward travel) is correlated with the speed of rotation of the spin rails so that a roller makes at least one full revolution, and preferably several, while the switch is open.

This timing of the variable reluctance test has been employed successfully for rollers whose lengths are slightly less than the length of the magnetic sections 11, 11'. As mentioned above, the variable reluctance test can be made during the forward travel of a roller, particularly for rollers whose length is greater than the length of magnetic sections 11, 11'. In such case reed switch 108 may be replaced by a pair of reed switches connected in series and suitably spaced longitudinally of the air cylinder to enable flaw threshold circuits 104 only during the interval the roller under test is in the magnetic field of sections 11, 11'. In general, the interval will correspond to the length of the roller minus the length of the magnetic sections for long rollers.

From the preceding explanation, and particularly from FIG. 6, it will be understood that a number of rollers intervene between the test station and the point of ejection into the segregating chute. Thus flaw signal storage and roller counting means are employed so that flaw signals for a given roller are effective at the time of segregation. In the embodiment described, the rollers are advanced by one roller length at each actuation of the feed finger 62, and hence at each forward stroke of the air cylinder piston. A normally closed reed switch 109 applies +V to shift pulse generator 110 during the forward stroke. At the end of the forward stroke magnet ring 107 opens switch 109 so that the voltage to generator 110 goes low. As the retract stroke begins, switch 109 recloses and the change to +V actuates generator 110 to produce a shift pulse in line 111. With a dwell interval at the end of the forward stroke, the shift pulse occurs after the dwell interval.

Whenever flaw relay 95 is actuated, the resultant AC burst is rectified in 112 and actuates flip-flop 113 to its set state. The flip-flop is of the type which retains its set state until reset, for example, a so-called "JK" flip-flop. The pulse in line 111 occurring at the end of the test interval for the defective roller causing the flaw signal, resets FF 113 and enters the flaw signal into shift register 114. Successive shift pulses in line 111 transfer the flaw signal from stage to stage in shift register 114, synchronously with the intermittent movement of the defective roller toward the ejection point. The number of stages in the shift register is selected so that the flaw signal appears at its output and actuates relay 115 as the defective roller reaches the ejection point and is forced off the spin rails. Several output lines from different stages are provided, and selectable by switch 116, to accommodate different length rollers.

Similarly, if flaw relay 105 is actuated during the variable reluctance test, the resultant AC burst is rectified in 112' and sets flip-flop 113'. Shift pulses in line 111 then enter the flaw signal into shift register 114' and shift the flaw signal from stage to stage so that relay 115' is actuated as the defective roller reaches the ejection point.

As mentioned before, if a given roller shows flaws in both eddy current and variable reluctance tests, in this embodiment the defective roller is directed to the outlet chute 77 for eddy current rejects. Further, as a fail-safe feature, rollers are rejected if the operator fails to turn on the power to the test apparatus. These functions are performed with the aid of relays 117 and 117' which, when actuated, supply DC power from lines 118 to rotary solenoids 119, 121 to turn rotatable vanes 78 and 79 in the directions indicated by the arrows. Ballast lamps 122, 122' reduce the current surge through the rotary solenoids and, if desired, may be used to indicate which is energized.

DC power from line 123 is supplied through the normally closed (NC) contacts of relays 115 and 115' to actuate relay 117'. Thus if no flaws are detected for the roller then entering chute section 74, vane 78 will have been turned clockwise and the roller will pass into the accept chute 75. If either the DC or AC power has not been turned on, vanes 78 and 79 will remain as shown, and the roller will pass into the variable reluctance reject chute 76. With power on, if an eddy current flaw signal actuates relay 115, line 123 will be switched to the NO contact and actuate relay 117. Thus solenoid 119 will turn vane 79 counterclockwise and the roller will pass into the eddy current reject chute 77. Power in line 124 will be cut off, so that vane 78 will be in the position shown, whether or not relay 115' is actuated. If eddy current relay 115 is not actuated, but the variable reluctance test indicates a flaw, relay 115' will be actuated and will disconnect power supply line 124 from relay 117', thereby deenergizing solenoid 121 and allowing vane 78 to assume the position shown. Thus the roller will pass into variable reluctance reject chute 76.

Figure 9:
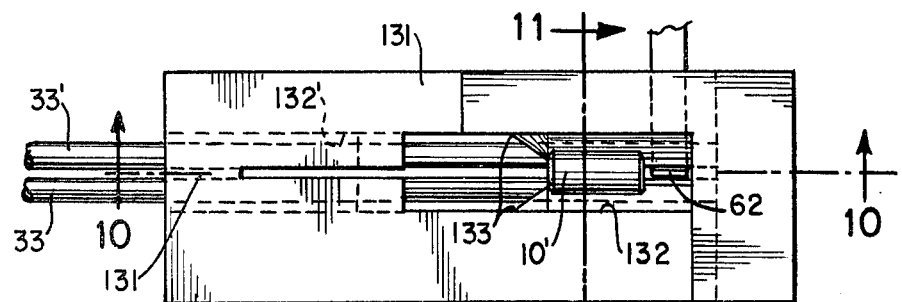
FIGS. 9, 10 and 11 are detail views in horizontal, vertical and lateral planes showing a modified slotted plate arrangement.
Figure 10:
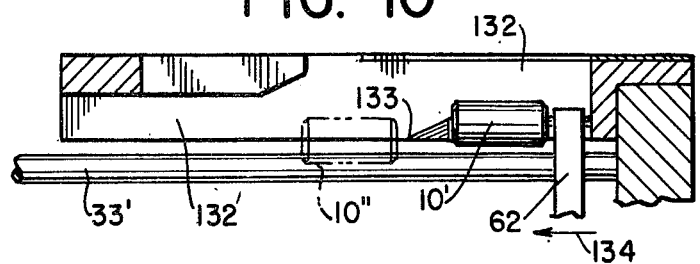
Figure 11:
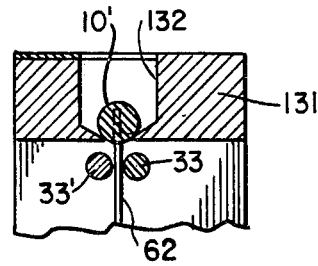

Referring now to FIGS. 9-11, a modification of the roller dropping and feeding mechanism is shown which is advantageous when testing rollers whose size and weight might result in marring their surface finish if dropped directly onto the spin rails, or might bounce excessively or unduly wear the spin rails. Instead of a plate 57 with a slot 58 allowing a roller to drop completely therethrough, as illustrated in FIG. 8, plate 131 has a slot 132 which is at least partially closed at the bottom so that, when a roller 10' is dropped into the slot by the feed head 45 (FIG. 8), it is supported somewhat above the spin rails 33, 33'. As here shown, a narrow opening in the bottom of the slot 132 allows feed finger 62 to pass therealong. The partially closed bottom terminates at point 133 in the direction of forward feed indicated by arrow 134, and the slot becomes full width in region 132' so that the roller drops onto the spin rails during the forward feed as indicated at 10". Advantageously the forward ends of the partially closed bottom are tapered outwardly and downwardly as shown, to drop the roller smoothly onto the spin rails. The partially closed bottom terminates ahead of the intermediate magnetic sections of the spin rails so that the roller is rotating smoothly when it reaches the test station.

Figure 12:
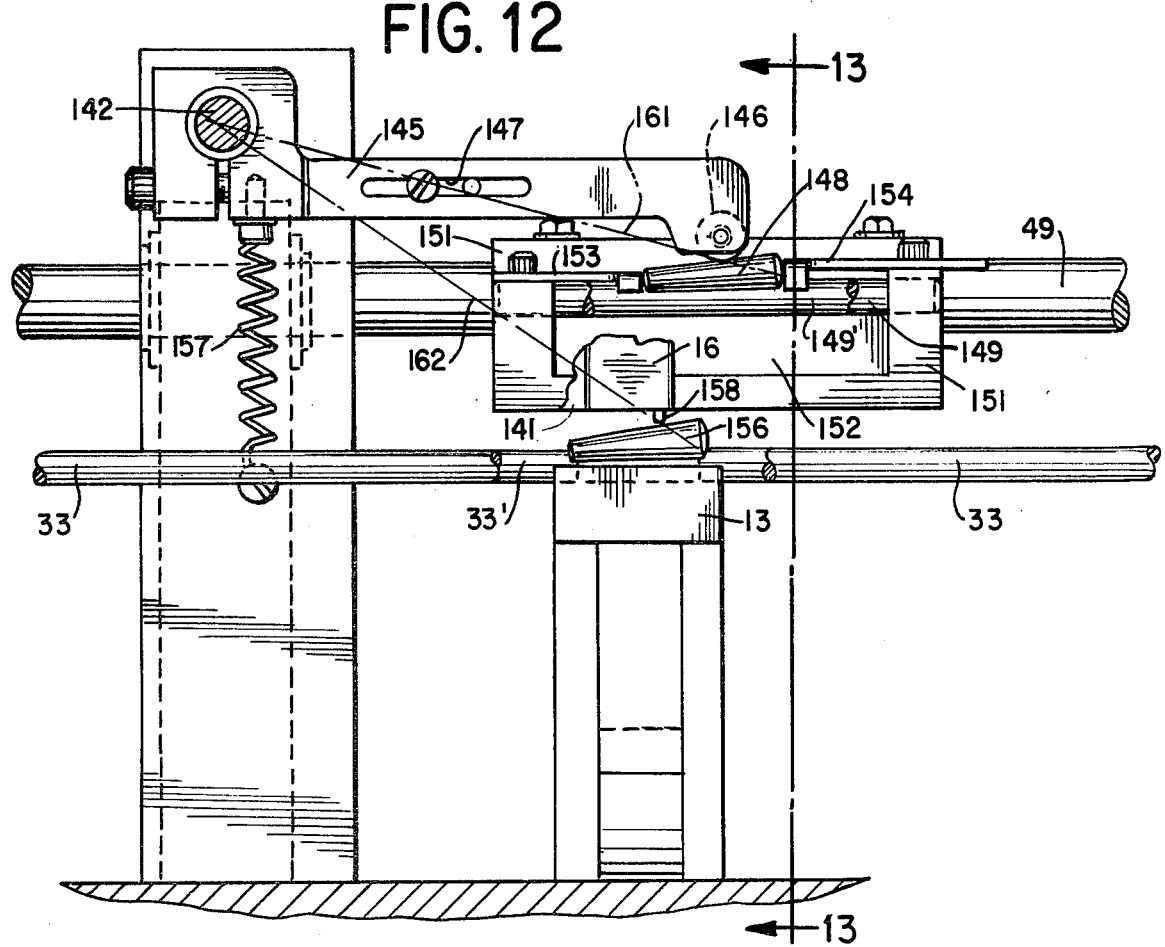
FIGS. 12, 13 and 14 are elevation, cross-section and plan views of a modification of the eddy current test probe arrangement for testing tapered rollers.
Figure 13:
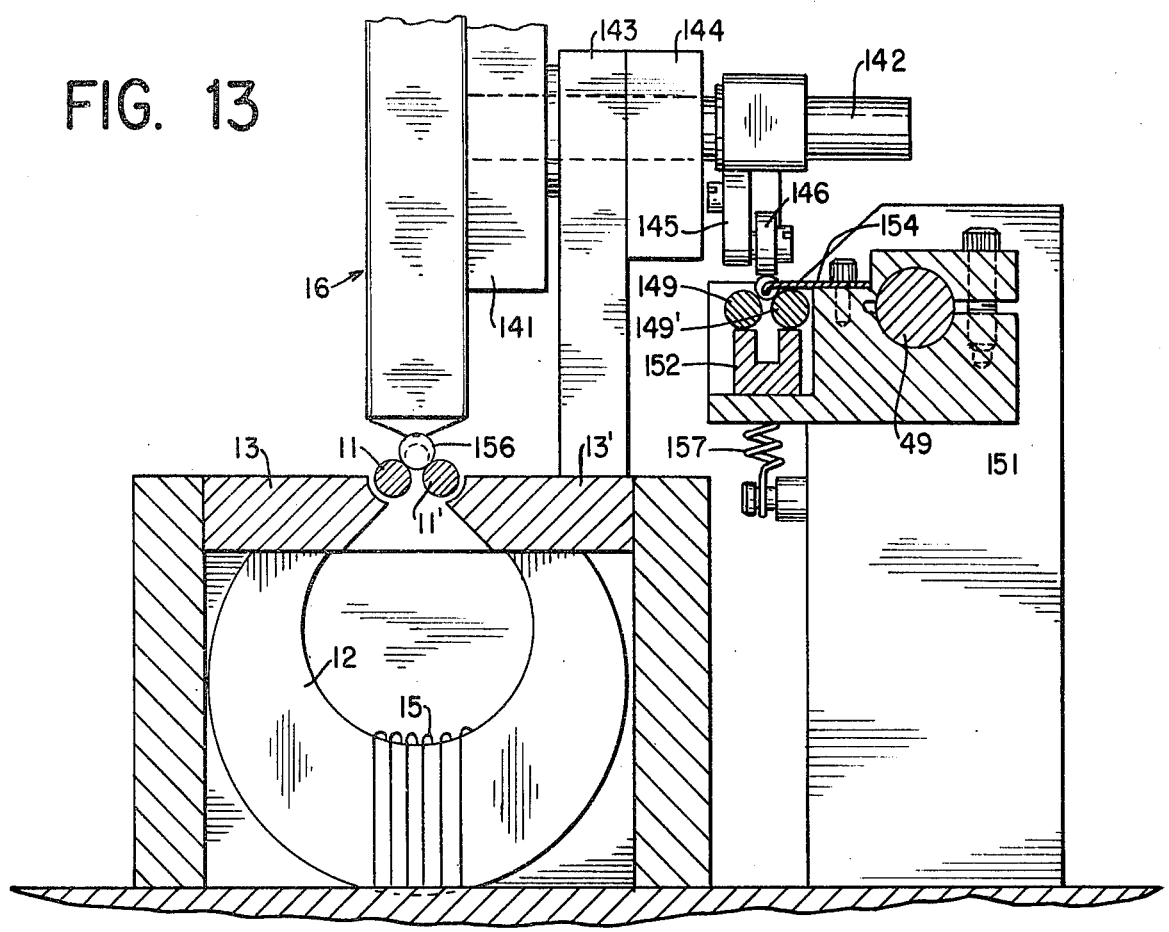
Figure 14:
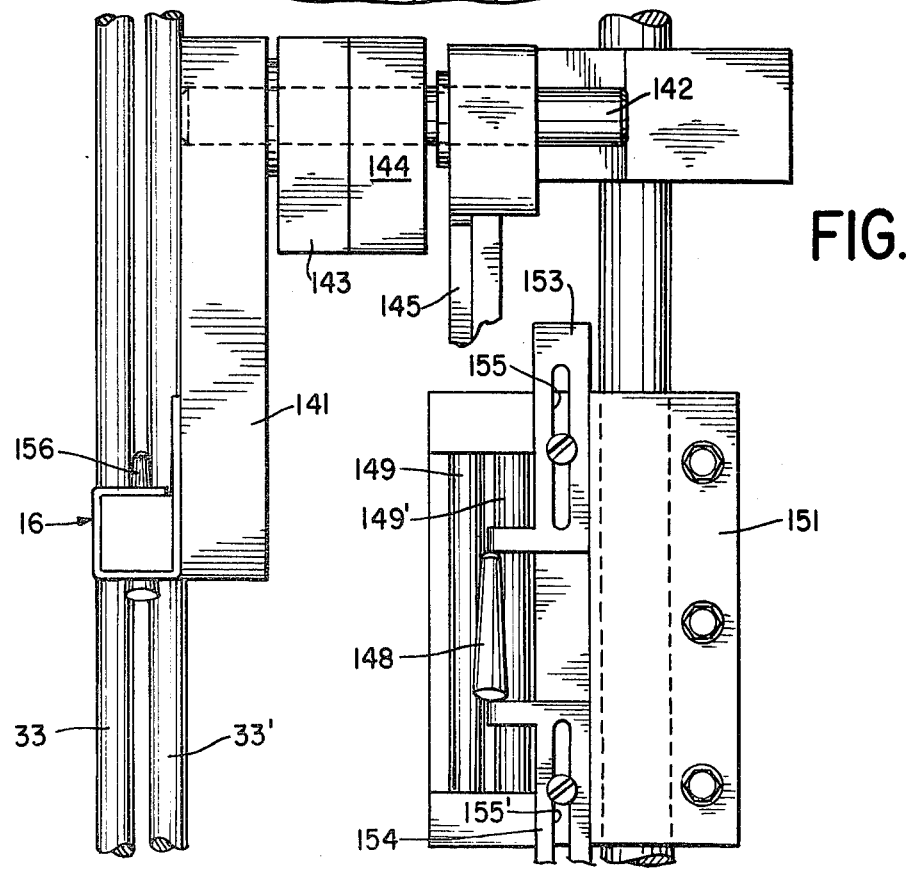

FIGS. 12-14 illustrate a modification which allows tapered rollers to be tested while preserving the sensitivity of the eddy current test along the length of the roller. In this modification means are provided for maintaining a constant spacing of the eddy current probe from the surface of the tapered roller as the roller is moved past the probe. To this end, mounting means for the probe is provided which is designed and adapted for moving the probe toward and away from a roller on the spin rails, and cam follower means is coupled with the mounting means and includes means for holding a guide tapered roller of like taper to rollers to be tested. Means are provided for producing relative movement between the guide tapered roller and the cam follower synchronously with movement of a roller past the probe to maintain constant the spacing between probe and roller.

Referring to FIGS. 12-14, the eddy current probe 16 is mounted on a plate 141 which is attached to a shaft 142 rotatable in bearing plates 143, 144. A cam arm 145 is attached to shaft 142 and carries a cam wheel 146. The cam arm is in two pieces and is adjustable in length by a pin and slot connection 147. A guide tapered roller 148 rests on two rods 149, 149' of magnetic material mounted on a carriage 151. The rods may be similar to the magnetic sections 11, 11' of the spin rails, but need not rotate. A channel horseshoe permanent magnet 152 mounted on carriage 151 produces magnetic flux through rods 149, 149' and guide roller 148 in a manner analogous to that shown in FIG. 1 so as to hold the tapered guide roller firmly against the rods. Guide roller 148 is also held between slide members 153, 154 adjustably mounted by pin and slot connections 155, 155' on carriage 151. Thus tapered guide rollers of various lengths corresponding to the tapered rollers 156 to be tested may be mounted on the carriage 151 and held in proper longitudinal position. Tension spring 157 biases cam arm 145 to hold cam wheel 146 in contact with guide roller 148.

Carriage 151 is attached to the piston rod 49 of the air cylinder so that guide roller 148 reciprocates longitudinally beneath cam wheel 146, thereby producing relative movement between the guide roller and the cam follower mechanism. Thus the cam arm 145 rotates shaft 142 and probe plate 141 so that, as cam wheel 146 moves along the inclined surface of guide roller 148, the spacing of probe 16 with respect to spin rails 33, 33' is changed and maintains constant the spacing between the probe and the tapered roller 156 under test.

With the tapered rollers oriented with their smaller diameter ends to the left, as shown in FIG. 12, at the beginning of the eddy current test the small end of roller 156 will be beneath the effective test region 158 of the probe, and cam wheel 146 will be riding on the small end of guide roller 148. As roller 156 is advanced during its forward feed (moved to the left as seen in FIG. 12), carriage 151 and the guide roller 148 will move to the left. Cam wheel 146 will ride on the inclined surface of guide roller 148 and move probe 16 upward, an intermediate position being shown in FIG. 12. This will continue until the large end of roller 156 has been reached. During the return stroke of piston rod 49, carriage 151 will move to the right, and cam wheel will ride down to the small end of guide roller 148, ready for the forward feed of the next roller to be tested.

By adjusting the length of cam arm 145, the radius from shaft 142 to the point of contact of cam wheel 146 with guide roller 148, indicated by dot-dash line 161, may be made equal to the radius from shaft 142 to the effective test region 158 of the probe, indicated by dot-dash line 162, for the size rollers being tested. Also the position of carriage 151 on piston rod 49 and the limits of travel of the piston rod may be adjusted so that test region 158 is at the desired point with respect to the feed of rollers under test.

The apparatus of FIGS. 12–14 may be modified by shortening arm 145 and attaching carriage 151 to piston rod 49 to the left of the position shown in FIG. 12, so that the cam wheel 146 is vertically over the effective test region 158 of the probe as viewed in FIG. 12. Also, the channel magnet 152 may be stationary as in the case of test magnet 12, and of suitable length to produce flux through rods 149, 149' and guide roller 148 for various lengths of rollers and various stroke lengths expected to be encountered in practice.

Inasmuch as there is an angle between lines 161 and 162 as seen in FIG. 12, the vertical components of movement of the cam contact with roller 146 and the probe will not be precisely the same. However, with small tapers of the rollers commonly encountered in practice and with adequately long arms, the error will usually be negligible since the sine varies almost exactly as the angle for small angles of movement. If desired, the probe plate 141 may be adjustable in length in the manner shown at 147 for the cam follower arm, and the position of cam wheel 146 may be vertically adjustable in the manner shown at 66 (FIG. 5) for the probe. With these adjustments, any significant errors may be reduced.

If desired, the position of carriage 151 may be changed so that guide roller 148 is in the same horizontal plane as the roller 156 under test, that is, in horizontal alignment as seen in FIG. 13, and the vertical angles indicated by dot-dash lines 161, 162 in FIG. 12 made the same, thus insuring equal vertical movements of cam wheel 146 and probe test area 158 and accurate maintenance of the spacing of the probe with respect to a roller under test.

The invention has been described in connection with specific embodiments having a number of features. It will be understood that certain features may be employed, and other features omitted or modified as meets the requirements of a particular application or the views of the designer.

We claim:

1. Non-destructive testing apparatus for rollers of magnetic material which comprises (a) a pair of rotating spin rails for rotating a roller placed thereon,
 (b) said spin rails having respective intermediate sections of magnetic material at like positions along the length thereof,
 (c) feeding means for depositing rollers on said spin rails and moving the rollers successively past said intermediate sections,
 (d) magnet means for producing magnetic flux through said intermediate sections and a roller rotating thereon,
 (e) variable reluctance sensing means for sensing changes in said flux,
 (f) an eddy current test probe positioned adjacent said intermediate sections for testing a roller rotating thereon,
 (g) variable reluctance and eddy current test circuits connected with said sensing means and probe, respectively, for producing respective flaw signals,
 (h) and segregating means for segregating the rollers in accordance with the presence or absence of flaw signals for respective rollers.

2. Apparatus according to claim 1 in which said magnet means is a permanent magnet and said variable reluctance sensing means includes a coil wound around the permanent magnet.

3. Apparatus according to claim 1 in which said feeding means intermittently deposits successive rollers on said spin rails and moves the rollers along the spin rails in end-to-end relationship, said segregating means including means for removing rollers successively from said spin rails beyond said intermediate sections, means for storing said flaw signals, and means responsive to a predetermined number of intermittent movements of the rollers along the spin rails for utilizing the stored flaw signals to segregate rollers as they are removed from the spin rails.

4. Apparatus according to claim 3 in which said means for removing rollers includes an inclined ramp between the spin rails for raising a roller as it is moved along the rails and an angled member for deflecting a raised roller off the spin rails.

5. Apparatus according to claim 1 in which said feeding means includes a plate having a slot therein extending longitudinally over said spin rails, a movable feed head over said plate having a channel closed at one end and open at the bottom, said feed head having respective receiving and feeding positions in which said channel is respectively away from and over said slot, supply means aligned with said channel in said receiving position for supplying rollers longitudinally into the channel to abut the closed end thereof, and means for alternately moving said head between receiving and feeding positions to drop received rollers into said slot in succession.

6. Apparatus according to claim 5 in which the width of said slot is predetermined to allow a roller to drop therethrough onto said spin rails, and including a feed finger for intermittently advancing rollers dropped onto the spin rails.

7. Apparatus according to claim 6 in which said feed finger extends upwardy between said spin rails.

8. Apparatus according to claim 5 in which said slot is at least partially closed at the bottom to support a roller above the spin rails, the at least partially closed bottom terminating ahead of said intermediate sections to allow a roller to drop onto the spin rails, and including a feed finger for intermittently advancing rollers from the bottom of the slot onto the spin rails.

9. Apparatus according to claim 5 in which said feed head is carried by a pivotally mounted arm and said means for alternately moving the head between receiving and feeding positions includes a reciprocally driven rod having cam means mounted thereon for engaging and moving said arm, and in which said feeding means includes a carriage reciprocally driven by said rod and carrying a feed finger extending upwardly between said spin rails for intermittently advancing rollers dropped into said slot.

10. Apparatus according to claim 1 in which said feeding means includes reciprocating means for intermittently advancing rollers along said spin rails in end-to-end relationship, and including means for enabling said eddy current test circuit to produce flaw signals during the forward movement of said reciprocating means which advances a roller past said probe and inhibiting the eddy current test circuit during the reverse movement of the reciprocating means.

11. Apparatus according to claim 10 including means for inhibiting said variable reluctance test circuit during the forward movement of said reciprocating means and enabling the circuit during predetermined intervals between forward movements.

12. Apparatus according to claim 1 for testing tapered rollers, including mounting means for said eddy current probe designed and adapted for moving the probe toward and away from a roller on the spin rails, cam follower means coupled with said mounting means and including means for holding a guide tapered roller of like taper to rollers to be tested, and means for producing relative movement between said guide tapered roller and said cam follower synchronously with movement of a roller past said probe for maintaining a substantially constant spacing of the probe with respect to the roller under test.

13. Apparatus according to claim 1 for testing tapered rollers including mounting means for said eddy current probe rotatable about an axis transverse to said spin rails and spaced from the probe, a cam follower arm rotatable about said axis and carrying a cam follower spaced therefrom, a carriage movable simultaneously with the movement of a roller past said probe, and means for mounting on said carriage in position for engagement by said cam follower a guide tapered roller of like taper to rollers to be tested, said mounting means for the probe and said cam follower arm being coupled for simultaneous movement about said axis for maintaining a substantially constant spacing of the probe with respect to a roller under test.

14. Non-destructive testing apparatus for rollers of magnetic material which comprises
 (a) a pair of rotating spin rails for rotating a roller placed thereon,
 (b) said spin rails having end sections of non-magnetic material with respective intermediate sections of magnetic material at like positions along the length thereof,
 (c) feeding means for intermittently depositing rollers in succession on adjacent ends of the spin rails and advancing the rollers along the spin rails in end-to-end relationship past said intermediate sections to the opposite end sections,
 (d) means for removing rollers successively from said opposite end sections of the spin rails,
 (e) a permanent magnet adjacent said intermediate sections for producing magnetic flux through the intermediate sections and a roller rotating thereon,
 (f) variable reluctance sensing means including a coil wound around the permanent magnet,
 (g) an eddy current test probe positioned adjacent said intermediate sections for testing a roller rotating thereon,
 (h) variable reluctance and eddy current test circuits connected with said coil and probe, respectively, for producing flaw signals,
 (i) means for storing said flaw signals,
 (j) segregating means for segregating rollers removed from the spin rails,
 (k) and means responsive to a predetermined number of advancements of the rollers along the spin rails for utilizing the stored flaw signals to segregate rollers as they are removed from the spin rails.

15. Apparatus according to claim 14 in which said feeding means includes reciprocating means for intermittently advancing rollers along said spin rails in end-to-end relationship, and including means for enabling said eddy current test circuit to produce flaw signals during the forward movement of said reciprocating means which advances a roller past said probe and inhibiting the eddy current test circuit during the reverse movement of the reciprocating means.

16. Apparatus according to claim 15 including means for inhibiting said variable reluctance test circuit during the forward movement of said reciprocating means and enabling the circuit during predetermined intervals between forward movements.

* * * * *